(12) United States Patent
Nohara et al.

(10) Patent No.: US 7,189,372 B2
(45) Date of Patent: Mar. 13, 2007

(54) DISSAPATING METHOD AND DEVICE AND DISSIPATING DEVICE FOR VOLATILE COMPONENTS

(75) Inventors: Hidenori Nohara, Tokyo (JP); Masamoto Matsukane, Tochigi (JP); Yoshiaki Fujikura, Tochigi (JP)

(73) Assignee: Kao Corporation, Tokyo (JP)

( * ) Notice: Subject to any disclaimer, the term of this patent is extended or adjusted under 35 U.S.C. 154(b) by 378 days.

(21) Appl. No.: 10/204,447

(22) PCT Filed: Feb. 7, 2001

(86) PCT No.: PCT/JP01/00855

§ 371 (c)(1),
(2), (4) Date: Nov. 20, 2002

(87) PCT Pub. No.: WO01/64256

PCT Pub. Date: Sep. 7, 2001

(65) Prior Publication Data

US 2005/0031511 A1 Feb. 10, 2005

(30) Foreign Application Priority Data

Mar. 1, 2000 (JP) .............................. 2000-055405

(51) Int. Cl.
*A61L 9/00* (2006.01)
(52) U.S. Cl. ..................... 422/123; 422/120; 422/305
(58) Field of Classification Search .................. 422/4, 422/5, 120, 123, 305, 205
See application file for complete search history.

(56) References Cited

U.S. PATENT DOCUMENTS

| 3,593,496 | A | | 7/1971 | Merrill |
| 4,139,762 | A | * | 2/1979 | Pohrer et al. ............... 392/402 |
| 6,770,247 | B1 | * | 8/2004 | Romack et al. ............. 422/123 |

FOREIGN PATENT DOCUMENTS

| JP | 20224/1991 | 2/1991 |
| JP | 04 046633 | 4/1992 |
| JP | 46633/1992 | 4/1992 |
| JP | 6-134025 | 5/1994 |
| JP | 3025315 | 3/1996 |
| JP | 8-280785 | 10/1996 |
| JP | 9-56770 | 3/1997 |
| JP | 9-88358 | 3/1997 |
| JP | 10-15049 | 1/1998 |
| JP | 11-351619 | 12/1999 |

* cited by examiner

*Primary Examiner*—Krisanne Jastrzab
*Assistant Examiner*—Sean Conley
(74) *Attorney, Agent, or Firm*—Oblon, Spivak, McClelland, Maier & Neustadt, P.C.

(57) ABSTRACT

A method of diffusing a volatile component comprising mixing a volatile component from a volatile substance with air having a relative humidity of 70% or higher and diffusing the mixed vapor. A device for diffusing a volatile component comprises a volatile component volatilizing part (6) for volatilizing a volatile component from a volatile substance and a high-humidity air generating part (1) for generating high-humidity air, wherein the volatile component (B) volatilized from the volatile component volatilizing part (6) and the high-humidity air (A) generated from the high-humidity air generating part are mixed and diffused outside.

7 Claims, 3 Drawing Sheets

① : 1×10⁷  ② : 2×10⁷  ③ : 3×10⁷

① : 1×10⁷  ② : 2×10⁷  ③ : 3×10⁷

DISSAPATING METHOD AND DEVICE AND DISSIPATING DEVICE FOR VOLATILE COMPONENTS

TECHNICAL FIELD

Figure 1:
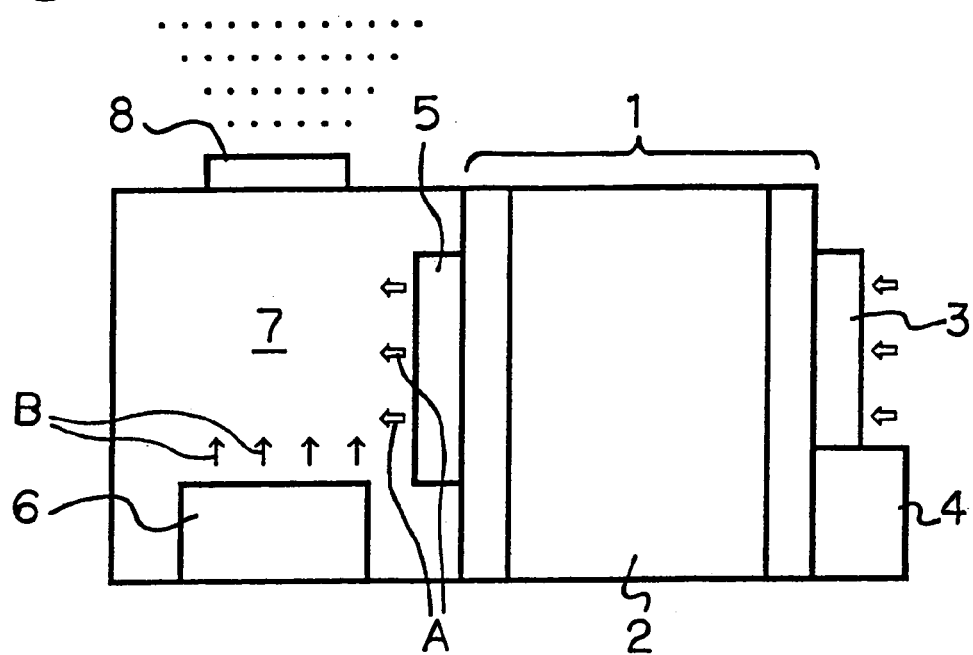

The present invention relates to a method and a device for diffusing volatile components from volatile substances, such as fragrances, to give off a smell that is qualitatively close to a natural smell.

The present invention also relates to a method of diffusing volatile components of volatile substances, such as fragrances, over a wide space efficiently.

BACKGROUND ART

It is known that fragrance of flowers, fruits, etc. affect humans favorably, providing mental relaxation and the like. Various fragrant preparations for spreading fragrance in a room have hitherto been developed. Perfume fragrances imitated from natural scents are commonly used as such fragrant preparations.

However, the fragrance given off from the conventional fragrant preparations is apt to be medicinal or overpowering smells that are felt artificial, failing to provide smells qualitatively equal to natural scents.

DISCLOSURE OF THE INVENTION

Accordingly, an object of the present invention is to provide a method and a device for diffusing volatile components of volatile substances, such as a fragrance, as a smell that is qualitatively close to a natural scent.

Another object of the present invention is to provide a method of diffusing a volatile component of a volatile substance, such as a fragrance, efficiently throughout a wide space.

The present invention accomplishes the above objects by providing a method of diffusing a volatile component which comprises mixing a volatile component from a volatile substance with air having a relative humidity of 70% or higher and diffusing the mixed vapor.

The present invention also accomplishes the above objects by providing a device for diffusing a volatile component which comprises a volatile component volatilizing part for volatilizing a volatile component from a volatile substance and a high-humidity air generating part for generating high-humidity air, the volatile component volatilized from the volatile component volatilizing part and the high-humidity air generated from the high-humidity air generating part being mixed and diffused into the outside.

The present invention also achieves the above objects by providing a method of diffusing a volatile component which comprises mixing a volatile component from a volatile substance with humidified air and diffusing the mixed vapor, wherein the volatile component and the humidified air are mixed to form volatile component-containing particles having a particle size of 1 µm or smaller (hereinafter referred to as a second aspect of the invention).

The term "volatile substance" as used herein is intended to include fragrances, such as natural fragrances and perfume fragrances, deodorants, and the like. The term "volatile component (from a volatile substance)" as used herein is intended to include various components volatilized from a volatile substance, such as fragrant components (perfume components), deodorant components, and the like. The present invention is particularly effective in diffusing various components from fragrances. The volatile substance is preferably made up solely of volatile components but may additionally contain non-volatile components.

The fragrance which can be used as a volatile substance includes various kinds customarily used in fragrant preparations, foods, cosmetics, etc., for example, natural perfumes extracted from natural matter, such as rose essential oil and peppermint essential oil, and synthetic perfumes artificially prepared, such as limonene and linalool.

Perfume fragrances prepared by compounding a plurality of known fragrance ingredients in an arbitrary mixing ratio are also useful. Subliming substances that are solid at ambient temperature, such as cedrol, are also employable. Further, aromatic plant parts, such as fruits, herbs, and trees, (including dried plant parts such as potpourri) also serve. The volatile components (aromatic components) to be volatilized from fragrances are not particularly limited as long as they are volatilizable from the fragrances.

BRIEF DESCRIPTION OF THE DRAWINGS

FIG. 1 is a schematic view illustrating the structure of a device for diffusing a volatile component according to a first embodiment of the present invention.

FIG. 2 is a schematic view illustrating the structure of a device for diffusing a volatile component according to a second embodiment of the present invention.

FIG. 3 is a schematic view showing the structure of a device for diffusing a volatile component according to a third embodiment of the present invention.

FIG. 4 is a diagram showing the volatile component concentration distribution in Example of the present invention.

FIG. 5 is a diagram showing the volatile component concentration distribution in Comparative Example concerning the second aspect of the invention.

BEST MODE FOR CARRYING OUT THE INVENTION

The present invention will be described in detail with reference to its preferred embodiments.

Embodiments of the volatile component diffusing device according to the present invention will be described by referring to FIGS. 1 and 2.

The volatile component diffusing device according to a first embodiment shown in FIG. 1 comprises a vapor mixing chamber 7 having a volatile component volatilizing part 6 for volatilizing a volatile component of a volatile substance and a discharge outlet 8; a high-humidity air generating part 1 having a high humidity area 2 containing supersaturated water vapor; and an air feeding means 3 which feeds air to the high humidity area 2 and leads high-humidity air A having passed through the high humidity area 2 to the vapor mixing chamber 7. The device is designed so that a volatile component B volatilized from the volatile component volatilizing part 6 is mixed with high-humidity air A introduced into the vapor mixing chamber 7 in the vapor mixing chamber 7 and then discharged outside from the discharge outlet 8.

The volatile component volatilizing part 6 is a part where a volatile component of a supplied volatile substance is volatilized. The device according to this embodiment has, in the vapor mixing chamber 7, a part (not shown) to which a volatile substance, such as a fragrance, is supplied so that the volatile component of the volatile substance supplied to this part may be gradually discharged from the volatile component volatilizing part 6 into the vapor mixing chamber 7. The volatilization mode of the volatile component may be any of spontaneous volatilization, volatilization by heat, ultrasonic volatilization, and the like.

The high-humidity air generating part 1 is a part where high-humidity air A is generated. In the device of the present embodiment, the part 1 is composed mainly of the high humidity area 2 in which water vapors are present in a supersaturated state without forming water droplets. The high humidity area 2 is formed of a water-retentive member made of a porous material such as sponge, which is set in the high-humidity air generating part 1, and impregnated with water. Air introduced from the outside becomes high-humidity air while flowing through pores inside the porous material or channels surrounded by the porous material.

The air feeding means 3 is a fan (not shown). On rotating the fan, outside air is let in, forcedly fed to the high humidity area 2, and made into high-humidity air A in the high humidity area 2, which is then led to the vapor mixing chamber 7. The high-humidity air led into the vapor mixing chamber 7 forms an air flow, whereby the volatile component B volatilized from the volatile component volatilizing part 6 and the high-humidity air A are mixed up. That is, the air feeding means 3 of the present embodiment also functions as a means for mixing the volatile component B and the high-humidity air A. The discharge outlet 8 of the vapor mixing chamber 7 is provided on the top of the vapor mixing chamber 7 as an opening of any shape, e.g., a circle or a rectangle.

In the present device, the volatile component volatilizing part 6 and the high-humidity air generating part 1 are independent of each other. A volatile substance and a source for generating air A (i.e., water or a water-containing liquid) are separately supplied to the volatile component volatilizing part 6 and the high-humidity air generating part 1, respectively, through separate routes.

More specifically, a fragrance as a volatile substance and water or a water-containing liquid as a source for generating high-humidity air are fed to the volatile component volatilizing part and the water-retentive member in the high-humidity air generating part 1, respectively, through respective feed routes so that the volatile substance and water, etc. as a source for generating high-humidity air are prevented from being mixed together in other situations than a vapor phase.

Since the device is so constructed as to supply a volatile substance and water or a water-containing liquid for generating high-humidity air through different routes, a natural smell can be easily obtained without involving the trouble of preparing a solution by using a surfactant for mixing a water-insoluble volatile substance with water as has conventionally been necessary.

The device of the first embodiment is equipped with a flow controlling means 5 for controlling the flow of the high-humidity air A introduced into the vapor mixing chamber 7. Specifically, a flow control fin capable of adjusting the size of its opening is provided as a flow controlling means 5 in the boundary between the high-humidity air generating part 1 and the vapor mixing chamber 7, the size of the opening of the flow control fin being adjusted to adjust the air flow. In FIG. 1, numeral 4 is a power source unit which supplies electricity to the air feeding means 3, etc. While it is sufficient for the diffusing device according to the present invention to have capability of generating humidified air having a higher humidity than that in the environment where the device is placed, it is preferred for the device to generate air having a relative humidity of 70% or higher at room temperature as high-humidity air to be mixed with a volatile component.

The method of diffusing a volatile component by use of the above-described volatile component diffusing device, i.e., a first embodiment of the volatile component diffusing method of the present invention will now be described.

First of all, a volatile substance such as a fragrance is supplied to the volatile component volatilizing part 6 to let the volatile component of the volatile substance volatilize from the volatile component volatilizing part 6. The water-retentive member in the high-humidity air generating part 1 is previously impregnated with water sufficiently.

The air feeding means 3 is then operated, whereby outside air is let in and fed to the high humidity area 2. Air fed to the high humidity area 2 becomes high-humidity air A while passing through the high humidity area 2 and is introduced into the vapor mixing chamber 7.

The volatile component B from the volatile substance is mixed with the high-humidity air A in the vapor mixing chamber 7, and the resulting mixed vapor is diffused through the discharge outlet 8 into the outside.

In the method of the present invention, the high-humidity air A mixed with the volatile component B from the volatile substance has a relative humidity of 70% or higher. The volatile component B from the volatile substance is mixed with high-humidity air A having a relative humidity of 70% or higher, preferably 80% or higher in the vapor phase, so as to make the diffused volatile component smell natural and felt extremely close to the smell of a natural substance. The relative humidity is measured at the temperature of the environment where the volatile component is to be diffused (usually 15 to 40° C.).

When measured with a light scattering particle counter, the mixed vapor of the volatile component B and the high-humidity air A is found to have particles, which are volatile component-containing particles produced by mixing the volatile component B and the high-humidity air A. The maximum particle diameter varied from 0.11 µm to 3 µm when measured under varied diffusion conditions such as humidity.

It has been ascertained that the smell becomes particularly natural when the volatile component is diffused under such conditions that volatile-containing particles having a particle diameter ranging from 0.11 to 0.5 µm are detected. That is, it is preferred in the present invention that the volatile component be diffused so that volatile component-containing particles having a particle diameter of 0.11 to 0.5 µm may be formed in the mixed vapor of the volatile component B and the high-humidity air A. As long as the volatile component-containing particles whose diameter ranges 0.11 to 0.5 µm are present, the vapor smells natural even through it contains particles out of this size range.

Particles having a particle size of 0.01 to 1 µm, which are called permanent suspended particles, float in space for a long time without sedimentation and are therefore preferred; for a natural smell slowly spreads in a room. They are also advantageous for safety, giving rise to no fear of dust diseases.

The rate of diffusion of the volatile component B/high-humidity air A mixed vapor is preferably 0 (corresponding to spontaneous convection by spontaneous volatilization) to 1 m/sec in terms of linear velocity at the discharge outlet 8.

The volatile component diffusing device according to the second embodiment and the volatile component diffusing method according to the second embodiment will then be described.

Figure 2:
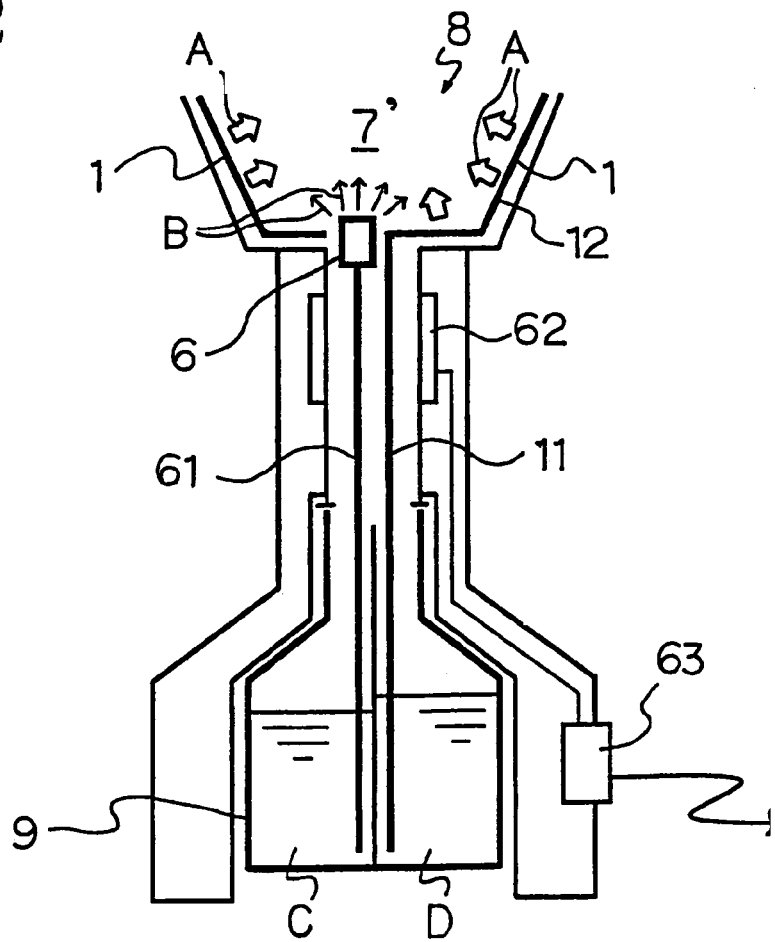

The volatile component diffusing device according to the second embodiment shown in FIG. 2 comprises a volatile component diffusing part 6 for volatilizing a volatile component of a volatile substance; a high-humidity air generating part 1 for generating high-humidity air; and a cup-like vapor mixing chamber 7' having a discharge outlet 8. The device is designed so that a volatile component B volatilized from the volatile component volatilizing part 6 and high-humidity air A generated from the high-humidity air generating part 1 are mixed in the vapor mixing chamber 7' and then discharged outside from the discharge outlet 8.

A volatile substance C containing a volatile component and water D or a water-containing liquid D as a source for generating high-humidity air are separately supplied to the volatile component volatilizing part 6 and the high-humidity air generating part 1, respectively, through independent routes.

That is, the volatile substance C contained in a container 9 is supplied to the volatile component volatilizing part 6 through a volatile substance feed tube 61 inserted in the container 9, and water D or a water-containing liquid D contained in the container 9 is supplied to the high-humidity air generating part 1 through a water feed tube 11 inserted in the container 9. The volatile substance feed tube 61 and the water feed tube 11 make the volatile substance C and water D, respectively, rise by capillarity. A heating unit 62 is provided in the middle of the feed tubes 61 and 11 so as to cause volatilization by heat. Numeral 63 in the Figure is a power for the heating unit 62. The mechanism for volatilization by heat may be replaced with spontaneous volatilization or a mechanism for ultrasonic volatilization.

The volatile substance C and the air-generating source D are set isolatedly from each other. That is, the volatile substance C and the water or water-containing liquid D, the source of high-humidity air generation, are set in the device in a non-mixed state.

The container 9 has an integral structure partitioned by a partitioning wall into a part for containing the volatile substance C and a part for containing the high-humidity air generating source D. The container 9 is removably fitted into the lower part of the device so that the device can easily be replenished with the volatile substance C and the high-humidity air generating source D by changing the container 9.

Since the volatile substance and the high-humidity air generating source are set in the device as isolated from each other, a natural smell can be easily obtained without involving the trouble of preparing a solution by using a surfactant for mixing a water-insoluble volatile substance with water as has conventionally been necessary.

In order to set the volatile substance and the air generating source isolatedly from each other, it is a preferred embodiment that they are separately placed in different parts of a container or different containers in a noncontact state. As long as the volatile substance and the air generating source can be taken out separately without being mixed together, they may be disposed in other forms, for example, they may be formed into different layers in a container.

The high-humidity air generating part 1 in the second embodiment is formed of a water-absorbing sheet (water-retentive member) 12, such as filter paper, which is disposed on the inner side of the cup-like vapor mixing chamber 7'. To the water-absorbing sheet 12 is connected the above-mentioned water feed tube 1 so that water may be always supplied to the water-absorbing sheet 12.

The volatile component volatilizing part 6 is exposed in the lower part of the vapor mixing chamber 7' without contact with the water-absorbing sheet 12. More specifically, the water-absorbing sheet 12 has a prescribed opening, and the volatile component volatilizing part 6 projects through the central part of the opening without contact with the periphery of the opening. In the second embodiment, too, the volatile component volatilizing part 6 and the high-humidity air generating part 1 are independent of each other, providing a structure that prevents the volatile substance C and water, etc. as an air generating source D from being mixed except in their vapor phase.

The heating unit 62 is a mixing means in the second embodiment. Heat by the heating unit causes convection in the vapor mixing chamber 7', whereby the volatile component B volatilized in the vapor mixing chamber 7' and the high-humidity air A generated in the vapor mixing chamber 7' are mixed up, and the mixed vapor is discharged outside through the discharge outlet 8. The vapor mixing chamber 7' and the upper discharge outlet 8 can each have an arbitrary shape, such as a circle and a rectangle. The other particulars of the device according to the second embodiment that are not described here are the same as those of the device of the first embodiment, and the explanation given to the first embodiment applies appropriately to the second embodiment.

The volatile component diffusing method by the use of the volatile component diffusing device of the second embodiment, i.e., the second embodiment of the diffusion method according to the present invention will be described hereunder.

First of all, the container 9 is fitted into the lower part of the diffusing device. A volatile substance and water in the container 9 are fed to the volatile component volatilizing part 6 and the high-humidity air generating part 1, respectively.

The volatile component volatilizes from the volatile component volatilizing part 6. On operating the heating unit 62, the volatilization is accelerated. The volatilization causes convection of surrounding air together with the volatile component, whereby the volatile component B is mixed with high-humidity air having a humidity of 70% or higher in the vicinity of the water-absorbing sheet 12 surface. The mixed vapor is diffused into the outside through the discharge outlet 8. The other particulars of the method according to the second embodiment that are not described here are the same as those of the method of the first embodiment, and the explanation given to the first embodiment applies appropriately to the second embodiment. For example, the preference in the first embodiment as for the particle size of the volatile component-containing particles, the linear velocity of diffusion, and the like applies to the second embodiment.

The high-humidity air having a relative humidity of 70% or higher which is to be mixed with the volatile component in the volatile component diffusing method of the present invention may be generated by evaporation and diffusion by heat, ultrasonic vaporization and the like, as well as a method of passing through a high humidity area. It is also possible that a flow of high-humidity air and a flow of relatively low humidity air are formed, the vapor from a volatile substance is introduced into the low-humidity air flow, and the low-humidity air and the high-humidity air are joined to mix the volatile component with the high-humidity air. The mixing means in the volatile component diffusing device of the invention is such that a volatile component vaporized from the volatile substance can be mixed with high-humidity air. For example, the air feeding means 3 in the first embodiment may be disposed in the vicinity of the discharge outlet 8 or the inlet of the vapor mixing chamber 7, and the air feeding means 3 may be disposed at two or more places. The volatile component volatilizing part can have any structure as is consistent with capability of volatilizing the volatile component of the volatile substance. The volatile substance, such as a fragrance, may be supplied to the volatile component volatilizing part by dropping a fragrance, etc. from the discharge outlet 8, etc. or by use of a tube, etc. The volatile substance may be supplemented or changed by using changeable containers, etc. as in the second embodiment. Further, the device may be designed to contain a certain amount of a fragrance in the volatile component volatilizing part so that the fragrance can be used in small portions on demand.

The third embodiment of the present invention (a preferred embodiment of the second aspect of the invention) is then described. A volatile component diffusing device which can be used with preference to carry out the diffusing method of the third embodiment is described first with reference to FIG. 3.

Figure 3:
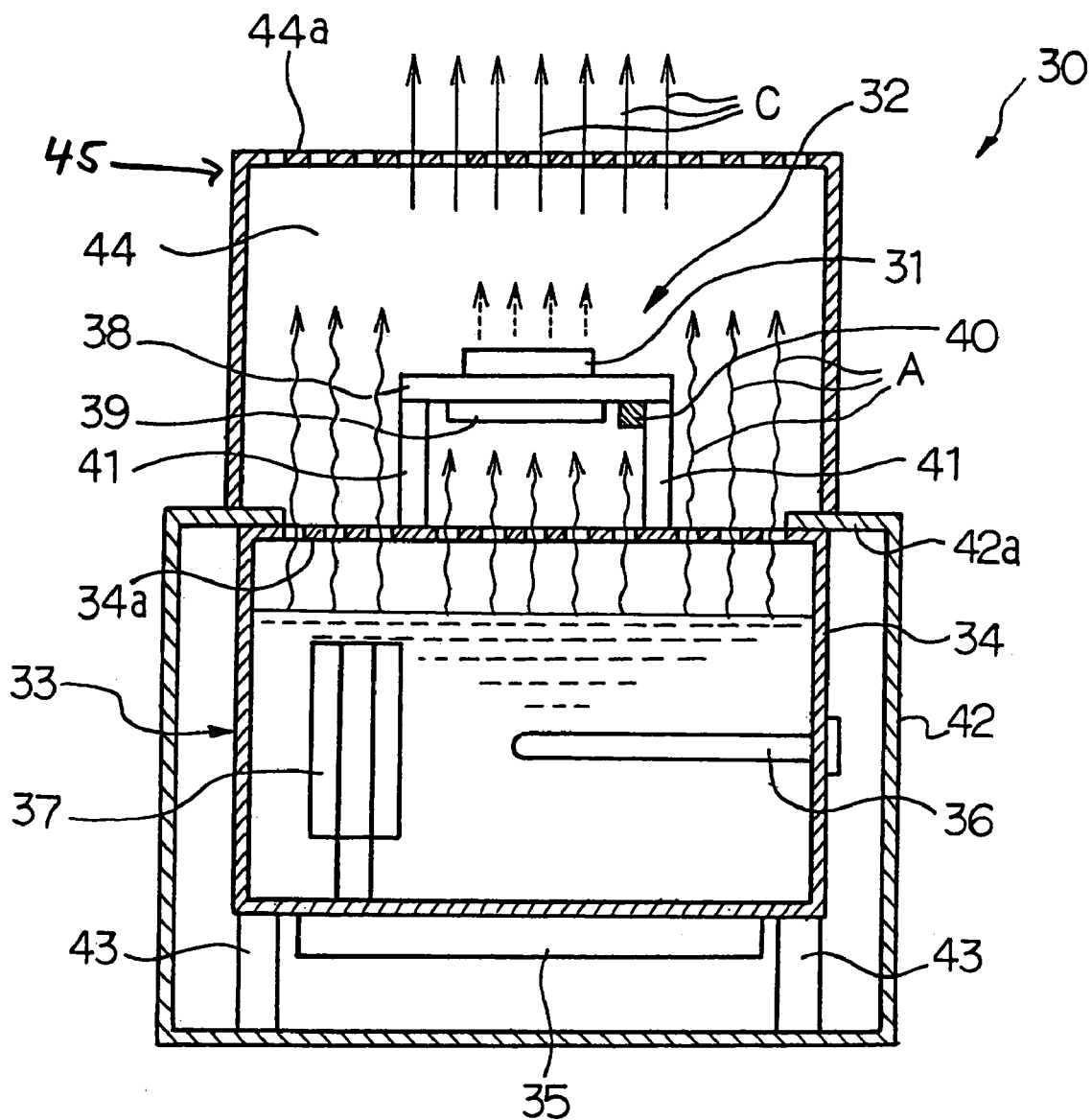

The volatile component diffusing device 30 shown in FIG. 3 comprises a volatilizing means 32 for heating a volatile substance 31 to volatilize a volatile component of the volatile substance; and a humidified air generating means 33 for heating water to generate humidified air (high-humidity air); wherein a volatile component B volatilized from the volatile substance 31 and humidified air A generated by the humidified air generating means are mixed in a vapor phase and diffused outside.

The humidified air generating means 33 has a water container 34 made of aluminum (12 cm (W)×12 cm (D)×8.6 cm (H)), a heating means 35 comprising a microceramic heater (AC 100 V, 100 W; 2.5 cm (W)×5 cm (L)) attached to the lower part of the water container 34; a heating temperature controlling means mainly comprising a K type thermocouple 36 attached to the side wall of the water container; and a float switch 37 for preventing dry operation which is provided in the water container 34.

A lid 34a is fitted to the top of the water container 34. The lid 34a has a large number of holes of 3 mm in diameter over the entire area thereof.

The volatilizing means 32 has a volatile substance mount 38 made of an aluminum plate; a volatile substance heating means 39 comprising a microceramic heater (100 V, 40 W) which is disposed on the lower side of the volatile substance mount 38; and a heating temperature controlling means mainly comprising a K type thermocouple 40 for monitoring the temperature of the volatile substance mount 38.

The volatile substance mount 38 is supported above the lid 34a by pillar insulators 40.

The volatile substance mount 38 is supported above the lid 34a by pillar insulators 41.

The top 42a of the case 42 has an opening of 16 cm in diameter so that humidified air A generated in the water container 34 is discharged into a vapor mixing chamber 44 through this opening and the holes of the lid 34a positioned within the opening.

The vapor mixing chamber 44 is formed by a bottomless box-shaped member 45 fitted onto the upper side of the case 42 so as to surround the opening of the top 42a of the case 42. A large number of holes having a diameter of 3 mm are bored in the top 44a of the chamber 44 to provide discharge outlets.

The volatile substance mount 38 is positioned in the central portion of the opening of the top 42a of the case 42 when viewed from above.

In carrying out diffusion of a volatile component (an aromatic component, etc.) by the use of the device 30, water is supplied to the water container 34 as a source of generating humidified air, and the volatile substance 31 is put on the volatile substance mount 38.

Water in the water container 34 is heated to a prescribed temperature by the heating means 35, whereupon water vaporizes to produce humidified air (high-humidity air). The thus produced humidified air A is led into the vapor mixing chamber 44.

The volatile substance mount 38 is heated to a prescribed temperature by the volatile substance heating means 39, whereupon the volatile substance 31 is heated to volatilize the volatile component therefrom.

The volatilized substance B from the volatile substance 31 is mixed with the humidified air A in the vapor mixing chamber 44 to make mixed vapor C, which is diffused into the outside through the discharge outlets made in the top 44a of the vapor mixing chamber 44.

By mixing the volatile component B and the humidified air A in the vapor mixing chamber 44, the diffused mixed vapor C contains volatile component-containing particles in which the volatile component B and the moisture content of the humidified air A are bonded.

Thus, in the volatile component diffusion method of the third embodiment, volatile component-containing particles having a particle diameter of 1 μm or smaller are formed by mixing the volatile component B from the volatile substance 31 and the humidified air A.

The volatile component from the volatile substance 31 is diffused outside in the form of volatile component-containing particles having a particle diameter of 1 μm or smaller and is thereby spread over wide space efficiently.

For achieving wide and efficient diffusion and wasteless use of the volatile substance, it is preferred for the mixed vapor C to have such a particle size distribution that the proportion of the total number of particles having particle diameters of 0.1 μm, 0.5 μm, and 1 μm to the total number of particles having particle diameters of 0.1 μm, 0.5 μm, 1 μm, 2 μm, and 5 μm is 10% or more, particularly 30% or more, especially 90% or more, as measured with a laser particle counter KA-13, supplied by Rion Co., Ltd. (measurement is made at a position of 50 cm above the volatile substance mount 38, which is 40 cm above the discharge outlets).

The volatile component-containing particles having a particle diameter of 1 μm or smaller can be formed by, for example, controlling the heating temperature for the volatile substance and that for the water as a humidified air generating source and appropriately controlling the volatilization rate (the amount of vapor generated per unit time) of the volatile component and that of the water.

By a proper choice of the water volatilization rate and the volatile component volatilization rate (former/latter), volatile component-containing particles having a particle diameter of 1 μm or smaller can easily be formed, and the proportion of particles of 1 μm or smaller can be increased.

While the device 30 shown in FIG. 3 adopts microceramic heaters as the water heating means 35 and the volatile substance heating means 39, each of them can be replaced with a silicone rubber heater, a nichrome wire heater, an infrared lamp heater, etc. Further, the volatile substance mount having a plate shape can be replaced with an open-top container having a depression in which a liquid or solid volatile substance may be put.

EXAMPLES

Example 1

A volatile component diffusing device shown in FIG. 1 was placed in a room having a temperature of 24° C. and a relative humidity of 50%. With a fragrance shown in Table 1 put in the diffusing device, the device was operated to diffuse the volatile components of the fragrance in the room. The quality of the smell drifting in the room was organoleptically evaluated by five panel members who were not particularly skilled in evaluating smells.

The organoleptic evaluation was made on a five-point scoring scale based on the following standard. a, b, c, d and e mean 5points, 4points, 3points, 2points, and 1point, respectively. The scores given by the five panel members were added up to give a total score. The results obtained are shown in Table 1.

The organoleptic test was repeated for each of the six fragrances shown in Table 1.

Comparative Example 1

The volatile components of a fragrance were diffused in a room in the same manner as in Example 1, except for replacing the diffusing device of FIG. 1 with a conventional device of thermal evaporation and diffusion type which does not involve water vaporization. The quality of the smell drifting in the room was organoleptically evaluated in the same manner. The results obtained are shown in Table 1.

Comparative Example 2

The volatile components of a fragrance were diffused in a room in the same manner as in Example 2, except for replacing the diffusing device of FIG. 2 with a conventional device of thermal evaporation and diffusion type which does not involve water vaporization. The quality of the smell drifting in the room was organoleptically evaluated in the same manner. The results obtained are shown in Table 2.

TABLE 1

| Example 1 | Volatile Substance | Panel Members | | | | | Score | Compara. Example 1 | Volatile Substance | Panel Members | | | | | Score |
|---|---|---|---|---|---|---|---|---|---|---|---|---|---|---|---|
| | | H | I | J | K | L | | | | H | I | J | K | L | |
| A | citrus fragrance | a | a | a | a | a | 25 | A | citrus fragrance | c | c | c | c | c | 15 |
| B | green fragrance | b | a | a | b | b | 22 | B | green fragrance | c | c | c | c | c | 15 |
| C | fruity fragrance | a | b | b | b | a | 22 | C | fruity fragrance | c | c | c | c | c | 15 |
| D | floral fragrance | b | a | b | b | a | 22 | D | floral fragrance | c | c | c | c | c | 15 |
| E | floral green fragrance | a | b | b | a | a | 23 | E | floral green fragrance | c | c | c | c | c | 15 |
| | woody fragrance | b | b | a | b | a | 22 | F | woody fragrance | c | c | c | c | c | 15 |

TABLE 2

| Example 2 | Volatile Substance | Panel Members | | | | | Score | Compara. Example 2 | Volatile Substance | Panel Members | | | | | Score |
|---|---|---|---|---|---|---|---|---|---|---|---|---|---|---|---|
| | | H | I | J | K | L | | | | H | I | J | K | L | |
| A | citrus fragrance | a | a | a | a | a | 25 | A | citrus fragrance | c | c | c | c | c | 15 |
| B | green fragrance | b | a | b | a | b | 22 | B | green fragrance | c | c | c | b | c | 16 |
| C | fruity fragrance | a | b | a | b | b | 22 | C | fruity fragrance | c | c | c | c | c | 15 |
| D | floral fragrance | a | b | b | b | a | 22 | D | floral fragrance | c | c | c | c | c | 15 |
| E | floral green fragrance | a | a | b | a | b | 23 | E | floral green fragrance | c | b | c | c | c | 16 |
| F | woody fragrance | b | b | b | a | a | 22 | F | woody fragrance | c | c | e | c | c | 14 |

Standard of Evaluation
  a: Particularly natural smell
  b: Natural smell
  c: Common smell
  d: Slightly unnatural smell
  e: Unnatural, artificial, and medicinal smell

Example 2

The volatile components of a fragrance were diffused in a room in the same manner as in Example 1, except for using the volatile component diffusing device of FIG. 2 in place of the diffusing device of FIG. 1. The quality of the smell drifting in the room was organoleptically evaluated in the same manner. The results obtained are shown in Table 2.

In Examples 1 and 2, the air introduced into the vapor mixing chamber 7 or the air generated in the vapor mixing chamber 7' had a relative humidity of 70% or higher. The mixed vapor at the discharge outlet was analyzed by a light scattering particle counter thereby to detect particles whose diameter fell within a range of 0.11 µm to 0.5 µm.

It is seen from the results shown in Tables 1 and 2 that the volatile components, etc. of fragrances diffused by the method and the device according to the invention are felt by the testers to be appreciably more natural and closer to the smell of a natural substance than those of the same fragrances diffused by a conventional method with a conventional device.

Example 3

A device having the structure shown in FIG. 3 was placed in a windless room (a wind velocity: less than 0.1 nm/sec) at a temperature of 25° C. and a relative humidity of 50%. A nonwoven fabric sheet impregnated with Dimetol, one of perfumery materials, was set on the volatile substance mount 38.

Dimetol (volatile substance, fragrance) and water in the water container 34 were separately heated to diffuse Dimetol (volatile component, aromatic component) in the room.

The volatile substance heating temperature (the set temperature of the plate) was 60° C., and the water heating temperature (set temperature) was 80° C.

As diffusion conditions, the water volatilization rate was 326 mg/min (at the set water temperature of 80° C.), and the Dimetol volatilization rate was 3 mg/min (at the set plate temperature of 60° C.).

Comparative Example 3

Dimetol was diffused in a room in the same manner as in Example 3, except that the device used in Example 3 was replaced with a device which has no humidified air generating means 33 but is instead designed to blow warm air at a prescribed temperature to the volatilizing means 32 from under the vapor mixing chamber. The temperature of the warm air was set at the same temperature of the water heating temperature in Example 3 (80° C.). The plate temperature was set at 60° C., and the Dimetol volatilization rate was 3 mg/min.

Measurement of Particle Diameter

The particle diameter distribution of the mixed vapor diffused from the device in Example 3 and Comparative Example 3 was measured by the aforementioned method (using a light scattering particle counter). The results obtained are shown in Table 3. The particles of Example 3 which belonged to the particle diameter sections of 1 μm and smaller are volatile component-containing particles of 1 μm or smaller.

Then the 4th to the n'th curves are $4 \times 10^7$, $5 \times 10^7$, $6 \times 10^7$ ... to $n \times 10^7$, respectively, wherein n is a natural number greater than 4.

The data on the negative side of horizontal distance D is a reproduction of equivalent data on the positive side.

Figure 4:
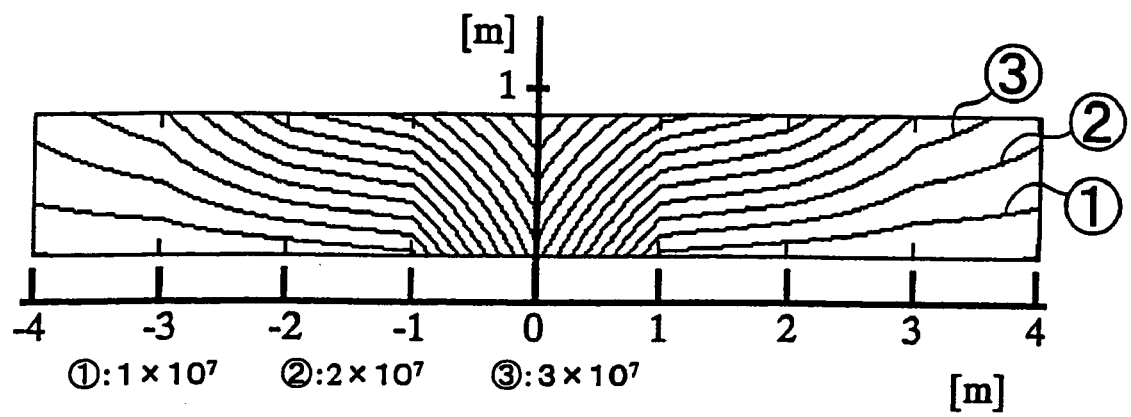
Figure 5:
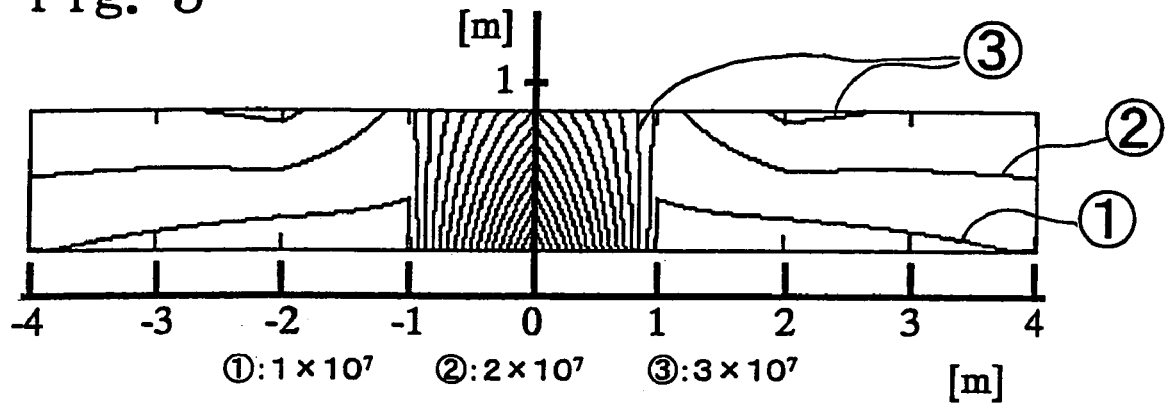

As can be seen from the results shown in FIG. 4, Dimetol, when diffused by the device (and the method) of Example 3, had high concentrations in the upper space and showed wide spread, indicating that the smell was drifting. To the contrary, in Comparative Example 3 wherein the mixed vapor contained particles similar in size to those observed in Example 3 but water vaporization was not involved, the concentration distribution was, as shown in FIG. 5, such that the concentrations around the device were high, and the concentrations in the lower space were higher than in Example 3, indicating that the vapor was crawling low on the floor without being diffused upward.

As demonstrated above, the device and the method of Example 3 successfully diffuse the volatile components (especially aromatic components) of a volatile substance more efficiently over a wider space than the device and the method of Comparative Example 3.

INDUSTRIAL APPLICABILITY

According to the volatile component diffusing method and device of the present invention, a volatile component from a volatile substance is diffused as mixed with high-humidity air to easily realize a natural smell that has been

TABLE 3

|  | Number of Particles (/l) | | | | | Ratio of Particles of Diameter of 0.3, 0.5, and 1 μm (%) | Ratio of Particles of Diameter of 2 μm and 5 μm (%) |
| --- | --- | --- | --- | --- | --- | --- | --- |
|  | Particle Diameter 0.3 μm | Particle Diameter 0.5 μm | Particle Diameter 1 μm | Particle Diameter 2 μm | Particle Diameter 5 μm | | |
| Example 3 | 14533 | 2549 | 870 | 334 | 92 | 98.5 | 1.5 |
| Comp. Example 3 | 10894 | 2035 | 662 | 244 | 55 | 97.8 | 2.2 |

Evaluation of Diffusion

Diffusion of Dimetol in Example 3 and Comparative Example 3 was evaluated as follows.

Air in the space in which Dimetol had been being diffused was sucked in a gas detector tube packed with an adsorbent TENAX TA at a rate of 0.5 l/min for 5 minutes from the start of diffusion. Sampling was conducted at 10 positions: 15 cm and 90 cm right above the discharge outlets (2 points); 1 m, 2 m, 3 m and 4 m distant from the center of the device in the hirizontal direction and 15 cm and 90 cm higher than the discharge outlets (8 positions).

The amount of Dimetol adsorbed in each of the gas detector tubes was analyzed on a gas chromatography/mass spectrometry instrument, supplied by Hewlett Packard, equipped with a thermal desorption system (TDS), supplied by Gerstel. Dimetol concentrations in the measuring points of the space were calculated. The Dimetol concentration distributions are shown in FIGS. 4 and 5, in which the horizontal distance D from the device is plotted as abscissa and the height H from the device as ordinate.

Each curve represents an isoconcentration curve (of an arbitrary unit concentration). For example, assuming that curve 1 is $1 \times 10^7$, curve 2 is $2 \times 10^7$, and curve 3 is $3 \times 10^7$.

regarded difficult to reproduce. For example, the smell of fragrances, etc. has been felt artificial, although fragrances are prepared by compounding techniques to imitate natural smells of flowers or fruits. According to the present invention, the smell of frangrances can be modified to what is felt particularly natural and close to a natural smell in quality.

According to the volatile component diffusing method of the present invention (second aspect), volatile components of volatile substances such as fragrances can be diffused efficiently and over a wide space.

The invention claimed is:

1. A device for diffusing a volatile component comprising:
    a volatile component volatizing part configured to volatize a volatile component from a volatile substance;
    a high-humidity air generating part configured to generate high-humidity air; and
    a vapor mixing chamber with a discharge outlet,
    wherein said volatile component volatized from said volatile component volatizing part and high-humidity air generated from said high-humidity air generating part is mixed in said vapor mixing chamber to form a mixed vapor, said vapor mixing chamber is configured to produce said mixed vapor having a particle size distribution such that the proportion of the total number of particles having particle diameters of 0.1 μm, 0.5 μm, and 1 μm to the total number of particles having particle diameters of 0.1 μm, 0.5 μm, 1 μm, 2 μm, and 5 μm is 10% or more, the mixed vapor is diffused into the outside through said discharge outlet, said volatile component volatizing part and said high humidity generating part are independent of each other, and said volatile substance and said air are supplied to said vapor mixing chamber from said volatile component volatizing part and said high-humidity air generating part, respectively, through separate routes.

2. The device for diffusing a volatile component according to claim 1, wherein the rate of diffusion of said mixed vapor of said volatile component and said high-humidity air is from 0 (corresponding to spontaneous convection by spontaneous volatilization) to 1 m/sec in terms of linear velocity at said discharge outlet.

3. The device for diffusing a volatile component according to claim 1, wherein said volatile substance and said source for generating part are isolated from each other.

4. The device for diffusing a volatile component according to claim 1, which further comprising a mixing means for mixing the volatile component volatized from said volatile component diffusing part and the high humidity air generated from said high humidity air generating part.

5. The device for diffusing a volatile component according to claim 1, wherein said high humidity air generating part generates air having a relative humidity of 70% or more.

6. The device for diffusing a volatile component according to claim 1, wherein said mixed vapor has a particle size distribution such that the proportion of the total number of particles having particle diameters of 0.1 μm, 0.5 μm, and 1 μm to the total number of particles having particle diameters of 0.1 μm, 0.5 μm, 1 μm, 2 μm and 5 μm is 30% or more.

7. The device for diffusing a volatile component according to claim 1, wherein said mixed vapor has a particle size distribution such that the proportion of the total number of particles having particle diameters of 0.1 μm, 0.5 μm, and 1 μm to the total number of particles having particle diameters of 0.1 μm, 0.5 μm, 1 μm, 2 μm, and 5 μm is 90% or more.

* * * * *